United States Patent [19]

Park et al.

[11] Patent Number: 5,578,240
[45] Date of Patent: Nov. 26, 1996

[54] COMPOSITIONS AND METHODS FOR IDENTIFYING A SOLUTION

[75] Inventors: John Y. Park, Santa Ana; James N. Cook, Mission Viejo; Anthony J. Dziabo, Jr., El Toro, all of Calif.

[73] Assignee: Allergan, Inc., Irvine, Calif.

[21] Appl. No.: 227,707

[22] Filed: Apr. 14, 1994

Related U.S. Application Data

[63] Continuation of Ser. No. 752,320, Aug. 30, 1991, abandoned.

[51] Int. Cl.$^6$ ................................................. C11D 17/00
[52] U.S. Cl. ...................... 510/513; 252/408.1; 424/471; 424/10.32; 510/112; 510/114; 510/513
[58] Field of Search ............................ 252/174, 174.12, 252/408.1; 424/471

[56] References Cited

U.S. PATENT DOCUMENTS

| | | |
|---|---|---|
| Re. 32,672 | 5/1988 | Huth et al. . |
| 4,568,517 | 2/1986 | Kaspar et al. . |
| 4,585,488 | 4/1986 | Giefer . |
| 4,767,559 | 8/1988 | Kruse et al. ........................ 252/90 |
| 4,852,591 | 8/1989 | Wisotzki et al. .................... 134/57 |
| 4,863,627 | 9/1989 | Davies . |
| 5,011,661 | 4/1991 | Schafer et al. .................... 422/30 |
| 5,382,599 | 1/1995 | Rupp et al. ........................ 514/547 |

FOREIGN PATENT DOCUMENTS

| | | |
|---|---|---|
| 0209071 | 1/1987 | European Pat. Off. . |
| 411887 | 2/1991 | European Pat. Off. . |
| 426489 | 5/1991 | European Pat. Off. . |
| 458578 | 11/1991 | European Pat. Off. . |
| 9112825 | 9/1991 | WIPO . |

OTHER PUBLICATIONS

Contactolgia, vol. 10D, 1988, Ph. Lapalus et al.: "Wirkung von Vitamin B12 auf die Abheilung von Hornhautwunden beim Kaninchen", pp. 73–75.
Spectrum, "Vitamins and Polymers in the Treatment of Ocular Surface Disease", pp. 37–42 (May 1990).
Holly, Frank J. "Vitamins and Polymers in the Treatment of Ocular Surface Disease" Spectrum (May 1990) pp. 37–42.

*Primary Examiner*—George Fourson
*Assistant Examiner*—C. Everhart
*Attorney, Agent, or Firm*—Jeffer, Mangels, Butler & Marmaro LLP

[57] ABSTRACT

A composition and method useful to quickly and effectively indicate whether a functional component such as catalase has been added to a clear solution such as a hydrogen peroxide solution involves compounding with the functional component an effective amount of vitamin B-12 such that when the compounded composition is added to the clear solution, the clear solution turns rose colored. By observing the rose color, the user can determine that the functional component has been added to the clear solution.

25 Claims, No Drawings

COMPOSITIONS AND METHODS FOR IDENTIFYING A SOLUTION

This application is a continuation of application Ser. No. 07/752,320, filed Aug. 30, 1991 now abandoned.

BACKGROUND OF THE INVENTION

This invention relates to ophthalmically safe compositions for identifying a solution. In particular, the present invention relates to compositions and methods useful to quickly and effectively facilitate the indication of the presence of an eye-irritating peroxide in a solution.

RELATED ART

Contact lenses are periodically cleaned and disinfected by the user to prevent infection or other deleterious effects on ocular health which may be associated with contact lens wear. Currently there are several different conventional systems and methods which enable the user to clean and disinfect contact lenses between wearing times. In one method the wearer removes the lenses from the wearer's eyes, and then performs a cleaning regimen using a solution containing a cleansing agent and a saline solution rinse. The lenses are then placed in a disinfecting solution for a suitable period of time, e.g., overnight, such that when the wearer awakens, the lenses have been cleaned and disinfected, ready for placement within the eye, preferably after rinsing again with saline solution. All of the mentioned solutions are clear, thus giving rise to the possibility of confusion among them.

Conventional cleaning and disinfecting systems can be divided into "hot" and "cold" systems. Hot systems require the use of heat to disinfect the contact lenses, whereas cold systems use chemical disinfectants at ambient temperatures to disinfect the lenses.

Within the realm of cold disinfectant systems are hydrogen peroxide disinfection systems. Disinfecting hydrogen peroxide solutions are effective to kill the bacteria and fungi which may contaminate contact lenses. Once the bacteria and fungi are killed, there is sometimes residual, unreacted hydrogen peroxide left in the solution. If the lenses are then removed from the solution, the lenses may have hydrogen peroxide on their surfaces. Such residual hydrogen peroxide on a disinfected contact lens may cause irritation, burning or trauma to the eye unless this hydrogen peroxide is neutralized. Therefore, neutralization of the residual hydrogen peroxide in the liquid medium containing the disinfected contact lens is needed to enable safe and comfortable wear of the disinfected contact lens.

Aqueous hydrogen peroxide-containing solutions currently in use as contact lens disinfectants include relatively high concentrations of hydrogen peroxide, for example, on the order of 3% weight to volume. Such high hydrogen peroxide concentrations are used so that the contact lens can be disinfected in a reasonable period of time, e.g., 10 minutes.

It would be advantageous to provide a contact lens disinfecting system in which it could be readily visually recognized when the residual peroxide is no longer present in the liquid medium containing the disinfected contact lens.

A typical contact lens cleaning regimen includes a clear saline solution, a clear daily cleaner, a clear disinfecting solution containing 3% hydrogen peroxide, and neutralizing tablets which contain the hydrogen peroxide neutralizer catalase. See U.S. Pat. No. 4,585,488 to Giefer.

In general, the regimen employs the following steps:
1. Cleaning the lenses with the clear sterile saline solution and the clear daily cleaner solution;
2. Placing the clean lenses in the clear disinfecting solution and allowing the lenses to soak for a minimum of 10 minutes to overnight; and
3. Adding to the clear solution the neutralizing tablets to neutralize any residual peroxide, the resulting solution also being clear.

One particular problem associated with this regimen arises from the fact that all of the solutions employed are clear. Thus, the solutions can be easily confused, especially if the wearer is tired. If the wearer is not aware that the wearer mistakenly neglects to neutralize the residual peroxide in the disinfecting solution, the wearer could take the lenses from the disinfecting solution and place them directly into the wearer's eye and thereby cause eye irritation. Since the disinfecting solution containing the residual peroxide and the solution containing neutralized peroxide are both clear, it is easy to mix up both solutions. It would therefore be advantageous to provide a contact lens disinfecting regimen whereby the wearer could readily visually differentiate between a solution containing peroxide and one which either contains no peroxide or one wherein the peroxide has been neutralized.

U.S. Pat. No. 4,863,627 to Davies discloses a contact lens disinfecting composition in solid form for addition to water which includes a contact lens disinfecting agent which is a source of hydrogen peroxide when in water, an inactivating agent to neutralize the hydrogen peroxide source, and a color change indicator such as phenolphthalein which changes from colored in solutions of hydrogen peroxide to colorless in essentially neutral solutions. Phenolphthalein, however, is incompatible with contact lenses as it stains the lenses upon soaking.

The May 1990 of *Spectrum* includes an article entitled "Vitamin and Polymers in the Treatment of Ocular Surface Disease" which describes an artificial tear formulation called "Nutratear" that contains approximately 0.05% (w/v) or approximately 500 ppm vitamin B-12. The article discloses that vitamin B-12 attributes a rosy color to the formulation, but the solution does not stain either clothing or contact lenses. The vitamin B-12 formulation is topically applied to the eye to provide relief from dry eye. Vitamin B-12 is also indicated as significantly reversing or even eliminating epithelial damage that is a commonly observed factor in ocular surface diseases.

Allergan France also distributes in France an artificial tear product called "Dulcis" which contains 0.05% vitamin B-12.

Various time release tablets having a core including a hydrogen peroxide-destroying component such as catalase and having a delayed release coating on the core are known. See for example Schafer et al. European Patent Application and Kaspar, U.S. Pat. No. 4,568,517.

SUMMARY OF THE INVENTION

The present invention is directed to an ophthalmically safe composition and method for identifying a solution, and more specifically to an ophthalmically safe composition and method for indicating the absence of residual peroxide in a solution resulting from the neutralization of peroxide in such solution by a peroxidase. The present invention utilizes the ophthalmically safe rose color inducing vitamin B-12 as an indicator.

Generally, the present invention involves an ophthalmic solution comprising a diluent such as water, an effective amount of vitamin B-12, and further including one selected from the group comprising a peroxide neutralizer, a cleanser, a disinfectant and a salt such as sodium chloride.

Another aspect of the invention involves an ophthalmic tablet comprising an effective amount of vitamin B-12 and a functional component such as, for example, a peroxide neutralizer, cleanser or disinfectant.

In a specific aspect of the present invention, an ophthalmically safe composition for indicating the presence of a peroxide is disclosed. The composition includes a peroxide neutralizing compound and vitamin B-12, preferably in tablet form and optionally coated with a time release coating.

In yet another aspect of the present invention, there is provided an ophthalmically safe method for indicating whether peroxide is present in a solution. The method comprises the steps of formulating a composition containing a peroxide neutralizing compound and an effective amount of vitamin B-12; adding the resulting composition to a solution containing peroxide; and observing the color of the solution.

DETAILED DESCRIPTION OF THE INVENTION

The present invention is of value where it is important to identify a specific solution and distinguish that solution from others used in an eye care regimen or other regimens where solutions come in contact with a living organism. The present invention is of particular value in facilitating the observation of a solution being free of peroxide.

The present invention takes advantage of the discovery that vitamin B-12 is ophthalmically safe and in solution is rose colored. Such rose color can act as an indicium of a solution in which vitamin B-12 is dissolved. By compounding vitamin B-12 with a functional component such as catalase or a disinfectant, one can readily determine whether the functional component has been added to a clear solution.

In one embodiment, the present invention involves use of vitamin B-12 as a safety indicator in lens care regimens which employ hydrogen peroxide. Specifically, in lens care regimens which employ hydrogen peroxide, the lens is typically placed in a solution containing approximately 10 mL of 3% weight to volume hydrogen peroxide. This solution is clear. After the lens is soaked in the hydrogen peroxide solution from 10 minutes to overnight, the lens is disinfected; however, there may be residual hydrogen peroxide left in the solution. The wearer, however, cannot tell whether such residual hydrogen peroxide is left as the solution remains clear.

In such a care regimen, the user will add to the solution a hydrogen peroxide neutralizing compound such as catalase. Typically the catalase is in aqueous solution or tablet form and optionally may be coated with a time release coating. Vitamin B-12 can be compounded in the tablet such that the tablet will contain the appropriate level of catalase to neutralize residual hydrogen peroxide and an amount of vitamin B-12 effective to change the color of the solution from clear to rose colored.

When the wearer adds the solution or tablet including catalase and vitamin B-12 to the solution containing residual hydrogen peroxide, the solution will become pink or rose colored. Such color will indicate to the user that a tablet containing a hydrogen peroxide neutralizing tablet has been added to the hydrogen peroxide solution containing the disinfected lens. Any suitable hydrogen peroxide neutralizing component may be included in the present compositions. Such hydrogen peroxide neutralizing component should effectively destroy the residual hydrogen peroxide and have no undue detrimental effect on the disinfected lens or on the eye into which the disinfected lens is placed. Among the useful hydrogen peroxide neutralizing components are hydrogen peroxide reducing agents, enzymes useful to destroy hydrogen peroxide, such as peroxidases and catalase, and mixtures thereof.

Examples of the hydrogen peroxide reducing agents which are useful in the present invention are alkali metals, in particular sodium sulfites; thiosulfates; thiourea; thioglycerol; N-acetylcysteine, alkali metal, in particular sodium, formates; ascorbic acid; isoascorbic acid; glyoxylic acid; pyruvic acid; ophthalmically acceptable salts, such as alkali metal and in particular sodium salts, of such acids; mixtures thereof and the like. A particularly useful hydrogen peroxide neutralizing component is catalase since it is often effective to substantially eliminate hydrogen peroxide from a liquid medium in a reasonable period of time, for example, on the order of about 1 minute to about 12 hours, preferably about 5 minutes to about 1 hour, after being initially released in the hydrogen peroxide containing media.

The amount of hydrogen peroxide neutralizing component employed is preferably sufficient to destroy all the hydrogen peroxide present in the hydrogen peroxide-containing media into which the hydrogen peroxide neutralizing component is placed. Excess hydrogen peroxide neutralizing component may be employed. Very large excesses of hydrogen peroxide neutralizing component are to be avoided since the hydrogen peroxide neutralizing component itself may cause problems with the disinfected contact lens and/or the ability to safely and comfortably wear such disinfected contact lens. When catalase is employed as a hydrogen peroxide neutralizing component, it is preferably present in an amount of about 100 to about 1000, more preferably about 150 to about 700, units of catalase activity per milliliter of liquid medium. For example, an especially useful amount of catalase for use in an aqueous solution containing about 3% (w/v) hydrogen peroxide is about 520 units of catalase activity/ml of solution.

The hydrogen peroxide neutralizing component may be combined with one or more other components, for example, in the core of tablet compounded according to the present invention. Such other components may include, for example, fillers, binders, tonicity agents, contact lens conditioning/wetting agents, buffering agents, lubricating agents and the like. Each of these components may be present, if at all, in an amount effective to perform its designated function or functions. Examples of each of these types of components are conventional and well known in the art. Therefore, a detailed description of such components is not presented here.

An illustrative tablet containing vitamin B-12 and a hydrogen peroxide neutralizing component may have the following composition:

| | Wt. % |
|---|---|
| Hydrogen Peroxide Neutralizing Component | 1–30 |
| Vitamin B-12 | 0.005–1.0 |
| Filler | 15–90 |
| Tonicity Agent | 1–90 |
| Buffering Agent | 1–50 |
| Lubricating Agent | 0–30 |

Useful tonicity agents include, but are not limited to, sodium chloride, potassium chloride, mannitol, dextrose, glycerin, propylene glycol and mixtures thereof.

Useful contact lens conditioning/wetting agents include, but are not limited to, polyvinyl alcohol, polyoxamers, polyvinyl pyrrolidone, hydroxypropyl methylcellulose and mixtures thereof. Certain of the present coating components as discussed below may provide one or more other useful functions after being dissolved in the hydrogen peroxide-containing media.

Typical saline solutions have a pH in the range of about 6 to 8 and include a buffer component which is present in an amount effective to maintain the pH of the saline solution in the desired range. Among the suitable buffer components or buffering agents which may be employed are those which are conventionally used in contact lens care products. Examples of use for buffer components include those with carbonate functionalities, bicarbonate functionalities, phosphate functionalities, borate functionalities, and the like and mixtures thereof. The buffers may be alkali metal and alkaline earth metal salts in particular sodium and potassium. Acids and bases may be used to adjust the pH of the present compositions as needed.

Useful lubricating agents include, but are not limited to, polyalkylene glycols, such as polyethylene glycols, preferably having molecular weights in the range of about 500 to about 10,000. Other materials conventionally used as lubricants in ophthalmically acceptable tablets may be employed in the tablet of the present invention.

The inclusion of one or more of such other components in the present compositions may be important to facilitate the functioning of such compositions and the present methods. For example, it may be desirable to maintain the pH and/or osmolality of the liquid aqueous medium within certain ranges, for example, to obtain preferred enzyme activities, coating component solubility and/or physiological acceptance. One or more of such other components may be included in the mixture which is applied to the core and which remain in the coating. Also, such other component or components may be included in the present compositions separate and apart from the coated core.

It should be appreciated that once a catalase tablet is added to a solution having residual hydrogen peroxide, the catalase reacts with the hydrogen peroxide to release oxygen. To the wearer what appears is a bubbling and frothing solution which gets somewhat warm. After the bubbling and frothing has subsided, the neutralization reaction between catalase and hydrogen peroxide is complete. The lenses may thereafter be safely placed within the eyes, although preferably first rinsed with an isotonic saline solution.

In another embodiment of the present invention, the vitamin B-12 can be added to virtually any ophthalmic solution in an amount which turns the solution pinkish or rose colored. In this manner, a particular solution can be identified and distinguished from other solutions. For example, an effective amount of vitamin B-12 can be added to an isotonic saline solution to thereby turn the solution pinkish color. In this way, the saline solution can be distinguished from other solutions. Vitamin B-12 can also be added to an aqueous peroxide-solution, peroxide-producing solid dosage forms such as perborates and persulfates, all-in-one cleaning and disinfection solutions and solid dosage forms, and generally to any chemical disinfection solutions and/or solid dosage forms, including all cleaning and/or disinfection solutions and tablets. Specific commercial examples include the addition of vitamin B-12 to Optifree™ (polyquaternary amine), ReNu™, Oxysept 1™ (hydrogen peroxide), Liquid Enzyme, Oxysept 2 (catalase), and Ultrazym™ and Heat Enzyme (subtilisin).

Alternatively, the vitamin B-12 can be added to a disinfecting solution which contains a chemical disinfectant such as Miramine or WSCP. For example, vitamin B-12 can be added to Allergan's® Hydrocare® Cleaning and Disinfecting Solution which contains 0.013% Miramine [tris (2-hydroxy-ethyl) tallow ammonium chloride]; 0.002% thimerosal; bis (2-hydroxy-ethyl) tallow ammonium chloride; sodium bicarbonate; sodium phosphate, dibasic, anhydrous; sodium phosphate, monobasic; propylene glycol; polysorbate, a polyhema; and hydrochloric acid in a sterile isotonic buffered solution. This solution then would become a rose colored solution which could be distinguished from normal isotonic saline solutions which would remain clear. Thus the present invention provides an ophthalmically safe method for identifying a solution by adding an effective amount of vitamin B-12 to the solution to change the color of the solution from clear to rose and observing the color of the resulting solution.

The vitamin B-12 that can be used for the present invention can be either cyanocobalamin or any cobalamin derivatives such as methylcobalamin, hydroxycobalamin, and desoxyadenosylcobalamin, provided such derivatives are ophthalmically safe and cause an aqueous solution to change observable color. Preferably cyanocobalamin is used.

The amount of vitamin B-12 used in connection with the embodiments of the present invention is at least that much which when dissolved in an aqueous solution will show an observable color change, and preferably a color change to rose or pink. In general, the amount of vitamin B-12 in solution will preferably range from 5 to 50 parts per million with 8 to 10 parts per million more preferred.

Without limiting the scope of the present invention, examples of hydrogen peroxide neutralizing tablets formulated according to the present invention are set forth below:

| Example 1 (No delayed release coating) | |
|---|---|
| INGREDIENTS MG/TABLET | |
| CATALASE CRYSTALLINE BOEHRINGER GRADE 1 | 1.5 |
| SODIUM CHLORIDE | 89.40 |
| SODIUM PHOSPHATE DIBASIC ANHYDROUS USP | 12.50 |
| POLYETHYLENE GLYCOL 3350 | 1.05 |
| SODIUM PHOSPHATE MONOBASIC MONOHYDRATE USP | 1.00 |
| CYANOCOBALAMIN | 0.081 |
| Example 2 (With delayed release coating) | |
| INGREDIENTS MG/TABLET | |
| CATALASE CRYSTALLINE BOEHRINGER GRADE 1 | 1.5 |
| SODIUM CHLORIDE | 89.40 |
| SODIUM PHOSPHATE DIBASIC ANHYDROUS USP | 12.50 |
| POLYETHYLENE GLYCOL 3350 | 1.05 |
| SODIUM PHOSPHATE MONOBASIC MONOHYDRATE USP | 1.00 |
| CYANOCOBALAMIN | 0.081 |
| METHOCEL E15LV PREMIUM (coating) | 5.00 |
| Example 3 (With delayed release coating and cleaning enzyme) | |
| INGREDIENTS MG/TABLET | |
| CATALASE CRYSTALLINE BOEHRINGER GRADE 1 | 1.5 |
| SODIUM CHLORIDE | 89.40 |
| SODIUM PHOSPHATE DIBASIC ANHYDROUS USP | 12.50 |
| POLYETHYLENE GLYCOL 3350 | 1.05 |
| SODIUM PHOSPHATE MONOBASIC MONOHYDRATE USP | 1.00 |
| CYANOCOBALAMIN | 0.081 |
| SUBTILISIN A (in the coating) | 0.0031 |
| METHOCEL E15LV PREMIUM (coating) | 5.00 |

The amount of catalase added was determined by an assay of the batch of product to be used. The above tablets prepared contained about 5200 units of catalase activity.

In a typical regimen, one tablet formulated according to the examples can be added to 10 ml of a 3% hydrogen peroxide solution after contact lenses have soaked for at least 10 minutes in the peroxide solution. After the bubbling of the resulting solution has subsided, e.g., about 10 minutes, the solution is pink and the lenses are disinfected yet relatively free of residual peroxide.

A time release coated tablet in accordance with Example 2 is used to disinfect a conventional soft contact lens as follows. 10 ml of a 3% (w/v) aqueous solution of hydrogen peroxide is provided at room temperature. The contact lens to be disinfected and the layered tablet are placed in the solution at the same time. For approximately ten (10) minutes, the solution remains substantially quiet, i.e., substantially no bubbling (gas evolution) takes place and the solution remains clear. For the next approximately 20 to 25 minutes, the solution bubbles. After this period of time, the solution becomes and remains quiet and the color of the solution changes to light rose color. Two hours after the contact lens is first introduced into the solution, it is removed from the solution and placed directly into the wearer's eye. It is found that after one hour, the contact lens is effectively disinfected. Also, the lens wearer experiences no discomfort or eye irritation from wearing the disinfected contact lens. The bubbling of the solution provides an indication that hydrogen peroxide destruction is occurring. An indication that the peroxide destruction is complete is provided when the bubbling stops and the solution is rose colored.

A coated tablet in accordance with Example 3 is used to disinfect and clean a protein-based debris laden soft contact lens as follows. 10 ml of a 3% (w/v) aqueous solution of hydrogen peroxide is provided at room temperature. The contact lens to be disinfected and cleaned, and the enzyme-containing coated tablet, are placed in the solution at the same time. For approximately ten (10) minutes the solution remains substantially quiet. For the next approximately 20 to 25 minutes, the solution bubbles and becomes pink. After this period of time, the solution becomes and remains quiet. Two hours after the contact lens is first introduced into the solution, it is removed from the solution, rinsed with physiological saline solution to remove the subtilisin A and placed into the wearer's eye. It is found that after one hour, the contact lens is effectively disinfected and cleaned of protein-based debris. The lens wearer experiences no discomfort or eye irritation from wearing the disinfected and cleaned contact lens.

The vitamin B-12 can be added directly to a solution, or may be present in a tablet as illustrated above in the form of, for example, a tablet, capsules, one or more solid particles and the like. Such a tablet includes a coated portion, for example, a core such as a core tablet containing the vitamin B-12 and for example, a catalase, and a barrier component coating. The barrier component can act to delay the release of the catalase and vitamin B-12 from the core portion for a period of time, preferably sufficient to allow the lens to be disinfected.

The delayed release of the vitamin B-12 and/or catalase into the liquid medium may be accomplished in any one of many suitable ways, a number of which are conventional and well known in the art. For example, the barrier component, for example a coating, may consist of a slowly dissolving coating material.

Barrier components suitable as either coating or as a matrix include water soluble vinyl polymers such as polyvinyl pyrrolidone, polyvinyl alcohol and polyethyleneglycol; water soluble protein; polysaccharide and cellulose derivatives such as methyl cellulose, hydroxypropyl methylcellulose, sodium carboxymethylcellulose; alginic acid and its salts and other derivatives; and the like and mixtures thereof.

The amount of barrier component used is not critical in the present invention provided that such barrier component functions as described herein. The barrier component or components may be suitably present in the range of about 1% to about 60%, based on the weight of the catalase and vitamin B-12.

A preferred delayed release coating or barrier coating is derived from a mixture comprising water, a ketone component and a water soluble coating component. This mixture is applied to the core containing the hydrogen peroxide neutralizing component in an amount sufficient to coat the core, in particular substantially all of the core, and form a precoated core. At least portions of the water and ketone component are removed from the precoated core to form the coated core, i.e., the core with a barrier coating.

The water soluble coating components useful in the present invention include those coating components which dissolve in water over a period of time. The coating component or components chosen for use should have no substantial detrimental effect on the lens being treated, on the disinfecting and cleaning of the lens, or on the person in whose eye the disinfected/cleaned lens is to be placed. The coating component or components used in the present barrier coatings and the amount or thickness of the barrier coating are preferably chosen so that the barrier coating dissolves into the hydrogen peroxide containing media after a period of time sufficient for the hydrogen peroxide to disinfect the lens located in the hydrogen peroxide-containing media.

The water soluble coating component or components may be chosen from ophthalmically acceptable materials, preferably polymeric materials, which function as described herein. Particularly useful coating components include water soluble cellulose derivatives, water soluble methacrylate-based polymers, water soluble vinyl pyrrolidone-based polymers and mixtures thereof. Mixed polymers of methyl vinyl ether and maleic acid anhydride, and polyvinyl alcohols can also be used.

The water soluble methacrylate-based polymers include polymers derived from methacrylic acid and/or methacrylic acid esters. Water soluble vinyl pyrrolidone-based polymers useful in the present invention include polymers derived in whole or in part from vinyl pyrrolidone, such as polyvinyl pyrrolidone, polyvinyl pyrrolidone derivatives, such as ethers and esters, and mixtures thereof. A specific example of useful water soluble vinyl pyrrolidone-based polymers is polyvinyl pyrrolidone acetate, such as the product sold by BASF under the trademark Kollidon VA-64. Water soluble methacrylate-based polymers, water soluble vinyl pyrrolidone polymers and mixtures thereof are quite useful.

The more preferred water soluble coating components comprise at least one water soluble cellulose derivative.

The water soluble cellulose derivatives useful in the present invention can be obtained by derivatizing cellulose to achieve the desired degree of water solubility. Substituent groups selected from hydrocarbon groups and substituted hydrocarbon groups are particularly useful for inclusion in the present cellulose derivatives. Such substituents which include 1 to about 10 carbon atoms, and such groups which include a polar group, such as a hydroxyl group, a carbonyl group, a carboxyl group and the like, are very effective in providing cellulose derivatives with the desired water solubility. Such water soluble cellulose derivatives can be produced using conventional and well known organic synthesis techniques.

The water soluble cellulose derivatives can be selected from water soluble cellulose ethers, water soluble cellulose esters and mixtures thereof, preferably water soluble cellulose ethers and mixtures thereof. Examples of water soluble cellulose esters include cellulose acetate phthalate, hydroxypropyl methylcellulose phthalate and the like.

Water soluble alkyl ethers and/or hydroxyalkyl ethers of cellulose are among the water soluble cellulose ethers which can be employed. The alkyl groups preferably have 1 to about 6, more preferably 1 to about 3 or 4, carbon atoms. Specific examples of useful water soluble cellulose ethers include hydroxypropyl methylcellulose, ethyl cellulose, methyl cellulose, hydroxyethylmethylcellulose, hydroxypropylcellulose, hydroxyethylcellulose, metal, in particular alkali metal, salts of cellulose ethers such as sodium carboxymethylcellulose, and the like and mixtures thereof. A particularly useful water soluble cellulose derivative is hydroxypropyl methylcellulose.

The ketone component or components useful are chosen to provide effective barrier coatings and to have no substantial adverse effect on the activity of the hydrogen peroxide neutralizing component, in particular catalase, or on the activity of the cleaning enzyme or enzymes, if any, present in the present composition. The ketone component or components have the characteristic ketone structure and are preferably selected from ketones having 3 to about 6 carbon atoms per molecule. The ketone component or components may include one or more substitutent groups provided that such group or groups do not substantially interfere with the functioning of the ketone component or components in the present invention. Specific examples of useful ketone components include acetone, methyl ethyl ketone, methyl isobutyl ketone and the like and mixtures thereof.

The relative amounts of water, ketone component, and water soluble coating component employed are preferably selected to achieve effective barrier coatings with little or no degradation in the activity of the hydrogen peroxide neutralizing component, and cleaning enzyme or enzymes, if present. More preferably, water is present in the mixture in a minor amount, i.e., less than about 50% (v/v), and the ketone component is present in the mixture in a major amount, i.e., more than about 50% (v/v), of the total amount of water and ketone component present in the mixture. Relatively high concentrations of water have been found to have a detrimental effect on the activity of the hydrogen peroxide neutralizing component, in particular catalase, in the item or items. For this reason, it is still more preferred to include no more than about 20% (v/v) water in the mixture. However sufficient water is preferably present in the mixture to insure that the water soluble coating components is completely solubilized in the mixture. With the coating component completely solubilized in the mixture, the barrier coating has good uniformity, for example, substantially uniform thickness, and has reliable and predictable delayed release characteristics. Coated cores produced from mixtures without water tend to have less uniform barrier coatings and to have less reliable and predictable delayed release characteristics.

The amount of water soluble coating component included in the mixture is such as to form a barrier coating on the core with the desired delayed release characteristics. Preferably, the amount of such coating component is such as to be completely solubilized in the mixture. In one embodiment, the amount of coating component present in the mixture is in the range of about 0.1% to about 20%, preferably about 0.2% to about 10% and more preferably about 0.5% to about 5%, (w/v) of the total mixture.

A particularly useful mixture includes 3% (w/v) of hydroxypropyl methylcellulose in a liquid medium of 90% (v/v) of acetone and 10% (v/v) of water.

The mixture may include one or more other components which act, for example, to facilitate applying the mixture to the core, to facilitate removing water and/or ketone component or components from the precoated core, and/or to provide a barrier coating with one or more useful properties and/or components which are useful to treat the lens when released in the hydrogen peroxide containing media. For example, the mixture may include one or more lubricating agents and/or deposit prevention agents to assist in maintaining the integrity of the barrier coating and to reduce deposit formation in the liquid aqueous medium in which the composition is used In certain instances, e.g., where the coating component is relatively hydroscopic, a final protective coating, for example, comprising one or more water soluble cellulose derivatives, may be applied to the coated or outer coated item or items, in particular using the method of the present invention, to protect the coated or outer coated item or items, such as during storage. This protective coating, which is often relatively thin, dissolves into the liquid aqueous medium very quickly, preferably substantially immediately, after the protected item or items are first contacted with the liquid aqueous medium.

The mixture, preferably a liquid solution, can be applied to the barrier coated core employing any conventional technique used, for example, to apply a liquid precursor of a delayed release coating to an item, such as a tablet, pill, microgranule, powder and the like. For example, the mixture can be sprayed onto the barrier coated core. Alternately, the barrier coated core can be dipped into the mixture. Conventional fluidized bed techniques can also be used.

The barrier coated core is subjected to conditions effective to remove, e.g., evaporate, at least a portion of the water and ketone component from the barrier coated core and form the coated core. Such conditions include, for example, ambient or slightly elevated temperatures.

In another embodiment of the present invention, vitamin B-12 can be added to a composition which is known to be effective to remove certain debris from a contact lens thus generating a rose colored solution when such compositions are employed in a liquid medium.

In a particularly useful embodiment, such compositions include at least one enzyme effective to remove debris from a contact lens. Among the types of debris that form on contact lens during normal use are protein-based debris, mucin-based debris, lipid-based debris and carbohydrate-based debris. One or more types of debris may be present on a single contact lens.

The enzyme employed may be selected from peroxide-active enzymes which are conventionally employed in the enzymatic cleaning of contact lenses. For example, many of the enzymes disclosed in Huth et al. U.S. Reissue Pat. No. 32,672 and Karageozian et al. U.S. Pat. No. 3,910,296 are useful in the present invention. These patents are incorporated in their entirety by reference herein. Among the useful enzymes are those selected from proteolytic enzymes, lipases and mixtures thereof.

A preferred group of proteolytic enzymes are the derived alkaline proteases generically called subtilisin enzymes. Reference is made to Keay, L., Moser, P. W. and Wildi, B. S., "Proteases of the Genus Bacillus. II Alkaline Proteases", Biotechnology and Bioengineering, Vol. XII, pp 213–249 (1970) and Keay, L. and Moser, P. W., "Differentiation of Alkaline Proteases from Bacillus Species" Biochemical and Biophysical Research Comm., Vol. 34, No. 5, pp. 600–604 (1969).

The subtilisin enzymes are broken down into two sub-classes, subtilisin A and subtilisin B. In the subtilisin A grouping are enzymes derived from such species as *B. subtilis, B. licheniformis* and *B. pumilis.* Organisms in this sub-class produce little or no neutral protease or amylase. The subtilisin B sub-class is made up of enzymes from such organisms as *B. subtilis, B. subtilis* var. *amylosacchariticus, B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collagenase, keratinase, carboxylase, aminopeptidase, elastase, and aspergillopeptidase A and B, pronase E (from *S. griseus*) and dispase (from *Bacillus polymyxa*).

An effective amount of enzyme is to be used in the practice of this aspect of the present invention. Such amount will be that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the extent of its interaction with the hydrogen peroxide present.

As a basic yardstick, the working solution should contain sufficient enzyme to provide about 0.001 to about 3 Anson units of activity, preferably about 0.01 to about 1 Anson unit, per single lens treatment. Higher or lower amounts may be used.

Enzyme activity is pH dependent so for any given enzyme, there is a particular pH range in which that enzyme will function best. The determination of such range can readily be done by known techniques.

In yet another aspect of the present invention, the vitamin B-12 can be added as an identifying color producing component to tablets or solutions containing disinfecting or antimicrobial agents. These agents include quaternary ammonium salts used in ophthalmic applications such as poly[(dimethyliminio)-2-butene-1, 4-diyl chloride, α-[4-tris(2-hydroxyethyl) ammonium-2-butenyl-w-tris(2-hydroxyethyl)ammonium]-dichloride (chemical registry number 75345-27-6), generally available as Polyquaternium 1® from ONYX Corporation, and benzalkonium halides, WSCP, WSCP/Croquat®, chlorine dioxide, and biguanides such as salts of alexidine, alexidine free base, salts of chlorohexidine, hexamethylene biguanides and their polymers. Croquat® is one of the quaternary ammonium salts that is based on a collagen hydrolysate of relatively low molecular weight. See U.S. Pat. No. 4,758,595 incorporated herein.

The salts of alexidine and chlorhexidine can be either organic or inorganic and are typically disinfecting nitrates, acetates, phosphates, sulphates, halides and the like. Preferred antimicrobial agents include the biguanides with hexamethylene biguanides, their polymers and water-soluble salts being most preferred. Generally, the hexamethylene biguanide polymers, also referred to as polyaminopropyl biguanide (PAPB), have molecular weights of up to about 100,000. Such compounds are known and are disclosed in U.S. Pat. No. 4,758,595 which is incorporated herein by reference.

Another compound which meets the foregoing criteria when detoxified is a compound having structural Formula A. See U.S. Pat. No. 4,029,817 assigned to Allergan, Inc. which is incorporated herein by reference.

wherein R is an alkyl or alkenyl radical having 12–20 carbon atoms and preferably a tallow radical, i.e., composed of mixtures of —$C_{17}H_{34}$ and —$C_{17}H_{35}$; and $R_1$, $R_2$, and $R_3$ are the same or different and represent alkyl radicals having 1–3 carbon atoms. This compound should be used together with a detoxifying amount of a non-toxic compound selected from the group consisting of water soluble polyhydroxyethyl methacrylate, carboxymethylcellulose, non-ionic surfactants such as polyoxyethylene sorbitan fatty acid esters and polyoxyethylene ethers, polyvinyl pyrrolidone, polyvinyl alcohol, hydroxypropyl methylcellulose and mixtures thereof.

The preferred compound of the above Formula A is alkyl triethanol ammonium chloride wherein the alkyl group is a tallow radical. This compound is known as Miramine TA-30® and is commercially available from the Miranol Chemical Company. The preferred compound can be obtained as a 30% aqueous acidic solution. The compound is fairly stable in acidic pH but tends to precipitate out of solution as the base under alkaline conditions.

The invention now being fully described, it will be apparent to one of ordinary skill in the art that many changes and modifications can be made without departing from the spirit or scope of the invention.

What is claimed is:

1. An ophthalmically acceptable single tablet composition for neutralizing residual peroxide in a solution and facilitating a visual indication of the absence of such peroxide in the solution after neutralization of peroxide, the composition comprising:

an amount from about 1 to 30 weight percent of a peroxide neutralizing compound sufficient to neutralize all of the residual peroxide; and an effective amount from about 0.005 to 1.0 weight percent of vitamin B-12, wherein the vitamin B-12 is released from the tablet such that the solution changes color from clear to rose as residual peroxide is neutralized.

2. The ophthalmically acceptable composition of claim 1 wherein the peroxide neutralizing compound is catalase.

3. The ophthalmically acceptable composition according to claim 1 further including a delayed release coating covering the catalase.

4. An ophthalmically safe method for identifying the absence of peroxide in a solution resulting from the completion of a peroxide neutralizing process in such solution by a peroxide neutralizing compound, the method comprising the steps of:

selecting an amount of peroxide to be neutralized;

formulating a single dosage composition comprising an amount from about 1 to 30 weight percent of a peroxide neutralizing compound sufficient to neutralize said amount of the peroxide and an effective amount from about 0.005 to 1.0 weight percent of vitamin B-12;

adding the resulting composition to a solution containing peroxide wherein the vitamin B-12 is released from the dosage such that the solution changes color from clear to rose as residual peroxide is neutralized;

observing the color of the solution; and waiting for a period of time of about 1 minute to 12 hours beginning at the time said solution is observed to change color from clear to rose.

5. The method of claim 4 wherein there is present from 5 to 50 ppm of vitamin B-12 added to the solution.

6. An ophthalmically safe single tablet composition for neutralizing residual peroxide in a solution and indicating the completion of the peroxide neutralization comprising:

an amount from about 1 to 30 weight percent of a peroxide neutralizer sufficient to neutralize all of the residual peroxide;

an effective amount from about 0.005 to 1.0 weight percent of vitamin B-12; and another component selected from the group consisting of a peroxide producing compound, a cleanser, a disinfecting agent and mixtures thereof, wherein the vitamin B-12 is released from the tablet such that the solution changes color from clear to rose as residual peroxide is neutralized.

7. The composition of claim 6 wherein a peroxide neutralizer is selected and the peroxide neutralizer is catalase.

8. The composition of claim 6 wherein a cleanser is selected and the cleanser is subtilisin A.

9. The composition according to claim 6 wherein a disinfecting agent is selected and the disinfecting agent is alkyl triethanol ammonium chloride wherein the alkyl group is a tallow radical.

10. The composition of claim 6 wherein the other component is hydrogen peroxide.

11. The composition of claim 6 wherein the other component is a quaternary ammonium salt.

12. The composition of claim 6 wherein the other component is sodium chloride.

13. The composition of claim 6 wherein the other component is a biguanide.

14. The composition of claim 6 wherein the other component is chlorine dioxide.

15. The composition of claim 6 wherein the other component is WSCP.

16. The composition of claim 6 wherein the other component is a mixture of WSCP and Croquat®.

17. The composition of claim 6 wherein the components are present in solid form.

18. The ophthalmically acceptable composition of claim 1 further comprising about 1 to 90 weight percent of a tonicity agent, about 1 to 50 weight percent of a buffering agent and up to about 30 weight percent of a lubricating agent.

19. The ophthalmically acceptable composition of claim 18 comprising about 1 to 30 weight percent of catalase, about 0.005 to 1.0 weight percent of vitamin B-12, about 1 to 90 weight percent of sodium chloride, about 1 to 50 weight percent of a buffering agent selected from the group consisting of sodium phosphate dibasic, sodium phosphate monobasic and mixtures thereof, and up to about 30 weight percent of polyethylene glycol.

20. The composition of claim 6 further comprising about 1 to 90 weight percent of a tonicity agent, about 1 to 50 weight percent of a buffering agent, up to about 30 weight percent of a lubricating agent, and an amount of an enzyme cleanser sufficient to provide about 0.001 to about 3 Anson units of activity per single lens treatment.

21. The ophthalmically acceptable composition of claim 20 comprising about 1 to 30 weight percent of catalase about 0.005 to 1.0 weight percent of vitamin B-12, about 1 to 90 weight percent of sodium chloride, about 1 to 50 weight percent of a buffering agent selected from the group consisting of sodium phosphate dibasic, sodium phosphate monobasic and mixtures thereof, up to about 30 weight percent of polyethylene glycol, and up to about 0.003 weight percent of subtilisin A.

22. An ophthalmically acceptable single tablet composition for neutralizing residual peroxide in a solution and facilitating a visual indication of the absence of such peroxide in the solution after neutralization of peroxide, the tablet composition comprising:

(a) a shell comprising an amount of a peroxide neutralizing compound sufficient to neutralize all of the residual peroxide; and (b) a core having a delayed release coating and comprising an effective amount of vitamin B-12, wherein the vitamin B-12 is released from the tablet such that the solution changes color from clear to rose only after substantially all of the residual peroxide is neutralized.

23. An ophthalmically safe method for identifying the absence of peroxide in a solution resulting from the completion of a peroxide neutralizing process in such solution by a peroxide neutralizing compound, the method comprising the steps of:

selecting an amount of peroxide to be neutralize;

formulating a single dosage composition comprising (a) a shell comprising an amount of peroxide neutralizing compound sufficient to neutralize said amount of the peroxide and (b) a core having a delayed release coating and comprising an effective amount of vitamin B-12;

adding the resulting composition to a solution containing peroxide wherein the vitamin B-12 is released from the dosage such that the solution changes color from clear to rose only after substantially all of the residual peroxide is neutralized; and observing the color of the solution.

24. An ophthalmically safe single tablet composition for neutralizing residual peroxide in a solution and indicating the completion of the peroxide neutralization comprising:

(a) a shell comprising an amount of a peroxide neutralizer sufficient to neutralize all of the residual peroxide;

(b) a core having a delayed release coating and comprising an effective amount of vitamin B-12; and (c) a component selected from the group consisting of a peroxide producing compound, a cleanser, a disinfecting agent and mixtures thereof, wherein the vitamin B-12 is released from the tablet such that the solution changes color from clear to rose only after residual peroxide is neutralized.

25. The ophthalmically acceptable composition of claim 19, comprising an amount of catalase sufficient to provide about 5200 units of activity per tablet, about 0.1 weight percent of vitamin B-12, about 85 weight percent of sodium chloride, about 12 weight percent of sodium phosphate dibasic, about 1 weight percent of sodium phosphate monobasic, and about 1 weight percent of polyethylene glycol.

* * * * *